United States Patent [19]
Groves, Jr.

[11] 3,959,323
[45] May 25, 1976

[54] OIL SOLUBLE MERCURY COMPOUND FOR AN ANALYTICAL STANDARD

[75] Inventor: William L. Groves, Jr., Ponca City, Okla.

[73] Assignee: Continental Oil Company, Ponca City, Okla.

[22] Filed: May 22, 1975

[21] Appl. No.: 579,760

[52] U.S. Cl............................ 260/402.5; 252/33.6
[51] Int. Cl.²................................... C07C 155/06
[58] Field of Search.................................. 260/402.5

[56] References Cited
UNITED STATES PATENTS

| | | | |
|---|---|---|---|
| 2,149,858 | 3/1939 | Miserentino | 260/402.5 |
| 2,304,369 | 12/1942 | Morgan et al. | 260/402.5 X |
| 2,693,447 | 11/1954 | Karll | 260/402.5 X |
| 2,925,781 | 2/1960 | Fischer | 260/402.5 X |

*Primary Examiner*—Patrick P. Garvin
*Attorney, Agent, or Firm*—Cortlan R. Schupbach, Jr.

[57] ABSTRACT

A stable oil-soluble metal carboxylate composition for use as an analytical standard for metal-in-oil analysis is provided. The composition is an equilibrium product represented as follows:

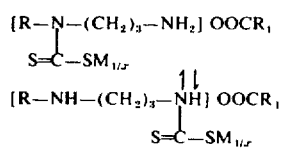

wherein M is a metal selected from the group consisting of mercury, vanadium, iron, lead, barium, berylium, tin, silver, titanium, copper, magnesium and sodium; R and $R_1$ are alkyl radicals containing from about 10 to 18 carbon and mixtures thereof; and, $x$ is an integer equal to the chemical valance of M.

6 Claims, No Drawings

OIL SOLUBLE MERCURY COMPOUND FOR AN ANALYTICAL STANDARD

BACKGROUND OF THE INVENTION

1. Field of the Invention

This invention relates to improved analytical standard compositions. In one aspect it relates to stable oil-soluble metal carboxylate compositions useful as analytical standards. In yet another aspect the invention relates to stable oil-soluble metal carboxylate analytical standards wherein the metal constituent is mercury vanadium, iron, lead, barium, berylium, tin, silver, titanium, copper, magnesium, sodium, or mixtures thereof.

2. Brief Description of the Prior Art

Dispersons containng certain oil-soluble metal salts have acquired considerable importance as additions in fuels and lubricating oil. Such dispersions have been highly useful as additives to other materials for the suspending of insluble waste materials formed in the utilization of the material and also for corrosion inhibition. When the oil-soluble metal salts are employed as additives for use in internal combustion engine lubricating compositions, such agents function to effectively disperse or peptize the insolubles formed by the fuel combustion, oil oxidation, or similar conditions obtained during the operation of the engine.

In recent years it has been found that superior standards for spectrographic equipment can be prepared from oil-soluble metal salts and metal dispersions of said salts by dissolving such materials in predetermined quantities in a suitable solvent. Such standards have exhibited indefinite shelf life and any combination of metals can be combined without precipitation of the metal constituents.

Thus, while the use of oil-soluble metal salts have been established and recognized, problems have been encountered in the production of stable oil-soluble metal salt compositions for use as an analytical standard for metal-in-oil analysis. Such problems have been even more prevelant in the production and use, as analytical standards, of oil-soluble metal carboxylate compositions of certain metals, such as mercury. For example, a number of oil-soluble mercury compounds have been made or proposed heretofore wherein such compounds are prepared from carboxylates, sulfonates, amines and alkylaryls; but, in all cases, the oil-soluble mercury compound is unstable as indicated by the formation of a grey precipitate.

Further, problems have been encountered in the blend stability of oil-soluble metal carboxylate compositions containing other metals such as molybdenum, vanadium, iron, boron and silver. Such problems have been especially encountered in the blend stability of such metal carboxylates at low metal concentrations, i.e. 100 parts per million or less. Therefore, a need has long been recognized for stable oil-soluble metal caboxylate compositions which can readily be used as analytical standards for metal-in-oil analysis.

OBJECTS OF THE INVENTION

An object of the present invention is to provide oil-soluble metal carboxylate compositions having improved stability.

Another object of the present invention is to provide stable oil-soluble metal carboxylate compositions which can be employed as analytical standards for metal-in-oil analysis.

Another object of the invention is to provide stable analytical standard for metal-in-oil analysis of mercury and other metals.

Yet another object of the invention is to provide an economical, dependable and efficient method for preparing stable oil-soluble metal carboxylate compositions.

These and other objects, advantages and features of the present invention will be apparent to those skilled in the art from a reading of the following detailed description.

DETAILED DESCRIPTION OF THE INVENTION

According to the present invention, I have now discovered a stable oil-soluble metal carboxylate composition which can be used as an analytical standard for metal-in-oil analysis. More specifically, the composition is a equilibrium product having the formula:

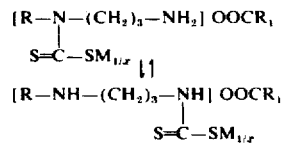

wherein M is a metal selected from the group consisting of mercury, vanadium, iron, lead, barium, berylium, tin, silver, titanium, copper, magnesium and sodium; R, and $R_1$ are alkyl radicals containing from about 10 to 18 carbon and mixtures thereof; and, $x$ is an integer equal to the chemical valance of M.

The stable oil-soluble metal carboxylate compositions described above can be prepared by adding to a reaction vessel, in the order shown, the following chemical compounds;

a. an alkyl diamine compound represented by the structural formula $R-NH-(CH_2)_3-NH_2$ wherein R is an alkyl radical containing from about 10 to 18 carbon atoms;

b. a diluent;

c. an alkyl substituted carboxylic acid having the structural formula $HOOCR_1$ wherein $R_1$ is an alkyl radical containing from about 10 to 18 carbon atoms;

d. carbon disulfide; and e. an organic metal salt;

It should be noted that each reaction is allowed to go to substantial completion before the addition of each sequential chemical compound. For example, the reaction between the alkyl diamine compound and the alkyl substituted carboxylic acid is allowed to be substantially complete before the carbon disulfide is added to the reaction mixture. Because of the viscous nature of the acid reactant the diluent is employed to facilitate mixing of the reactants. However, it is to be understood that the diluent is inert and does not chemically react with any of the reactants. To better understand the method of producing the stable oil-soluble metal carboxylate compositions of the present invention the following sequence of chemical reactions is set forth. In each reaction the chemical short hand, as to alkyl radicals and the like, is as previously described.

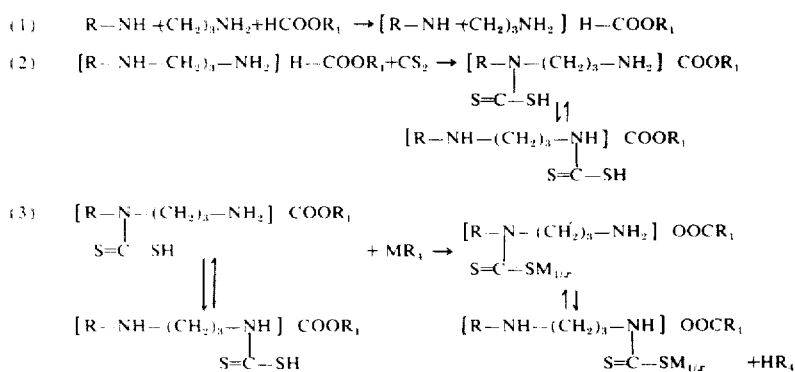

wherein $MR_1$ is an organic salt of the metal desired.

Once the desired product is produced, additional diluent can be admixed with the product, if desired, so that the product can more readily be filtered to remove insolubles formed during the reaction. The filtrate can then be diluted further to provide a solution containing a desired amount of the metal therein so that same can readily be employed as an analytical standard.

The amount of each constituent employed in the before mentioned chemical reactions can vary widely depending to a large extent on reaction conditions. However, in order to provide a stable product it is desirable that the alkyl substituted diamine and carboxylic acid constituent be employed in stiochemetric amounts. If an excess of the amine constituent is employed the product formed is less stable and on standing, a separation of the metal constituent can be detected by a decrease of the metal constituent in the sample.

As previously stated, the alkyl diamine compound can be any compound having the formula $R-NH-(CH_2)_3-NH_2$ wherein R is a alkyl radical containing from about 10 to 18 carbon atoms. However, especially desirable results have been obtained wherein the alkyl moiety is selected from the group consisting of n-coco, n-tallow, n-soya and n-oleyl.

The diluent employed is, as previously stated, an inert liquid which is employed to reduce the viscosity of the reaction mixture. The amount of diluent employed can vary widely and will be dependant on the viscosity of the reactants. Any suitable diluent can be employed, such as pale oil, kerosene, and the like.

The alkyl substituted carboxylic acid constituents employed to produce the oil-soluble sulfonate component are represented by the formula $HCOOR_1$ wherein $R_1$ is an alkyl radical containing from about 10 to 18 carbon atoms.

The carboxylic acid constituent can be a saturated carboxylic acid, or unsaturated carboxylic acid, and mixtures of same. Examples of saturated carboxylic acids useful in the preparation of the carboxylate composition of the present invention are lauric acid, myristic acid, palmitic acid, and stearic acid; unsaturated acids include linoleic, ricinoleic linolenic and oleic acid. The fatty carboxylic acids, which are normally available as mixtures, are derived from coconut oil, tall oil, tallow, and the like.

The reaction between the alkyl diamine compound and the carboxylic acid constituent is carried out at ambient temperature and pressure. However, the reaction mixture is agitated for a period of time sufficient to ensure substantial completion of the reacton between the diamine compound and the carboxylic acid. (See Equation 1).

Once the desired reaction product has been formed, a stoichiometric amount of carbon disulfide, based on, the reaction product of the diamine and carboxylic acid constituents is added to the reaction product. The resulting mixture is thoroughly agitated until the desired reaction, set forth in Equation 2, has occurred. Thereafter, an organic salt of a metal is admixed with the sulfur containing reaction product and the reaction allowed to proceed, under agitation, until the desired oil-soluble metal carboxylate has been formed. The reaction between the sulfur containing reaction product and the organic salt compound is an ion interchange reaction which is most effectively carried out under the influence of moderate temperature. Thus, it is desirable that the ion interchange reaction be carried out at a temperature in the range of from about 20° to 60° C.

As previously stated, the metal ion to be transferred can be mercury, vanadium, iron, lead, barium, berylium, tin, silver, titanium, copper, magnesium and sodium. However, the method for producing the desired oil-soluble metal carboxylate compositions of the invention is particularly effective when the metal ion to be transferred is mercury. Examples of suitable organic salts containing the desired metal ions, which can be employed to produce the compositions of the present invention are metal acetate materials such as mercuric acetate, cupric acetate, tributyltin acetate, silver acetate, lead acetate, tributylead acetate and the like.

In the formation of the oil-soluble metal carboxylate compositions of the present invention one may experience difficulties due to the low solubility of organic salts of certain metals. For example, when cupric acetate is employed as the salt constituent a solubilizer, such as methyl cellosolve, may be incorporated into the reaction mixture so that the before mentioned ion exchange reaction (Equation 3) can more efficiently proceed. While the amount of the solubilizer employed can vary widely, it is generally desirable that only sufficient solubilizer be incorporated to obtain miscibility of the organic salt with the reaction mixture. Solubilizers, which can be employed are well known in the art and include low molecular weight alcohols such as methanol, ethanol, isopropanol and the like; low molecular weight esters such as ethyl acetate; and low molecular weight ketones such as acetone, methylethyl ketone and the like.

The reaction product so formed is then diluted with from about 20 to 50 weight percent of an inert hydrocarbon diluent in which the oil-soluble metal carboxylate composition is soluble. The diluent, as previously described, is a petroleum derived diluent. Especially desirable results are obtained when the diluent is selected from the group consisting of pale oil and kerosene. The resulting solution is then purified to remove acid constituents formed during the ion interchange reaction. The purified product can then be further diluted with the diluent to produce a solution having a predetermined amount of the stable oil-soluble metal carboxylate compositions of the present invention. Preferably, the metal carboxylate constituent in the diluent will be present in an amount to provide less than 100 parts per million metal in the solution.

In order to more fully illustrate the nature of the present invention, the following experimental data is given. However, it is to be understood that the experimental data is for illustrative purposes only and are not intended to unduly limit or restrict the present invention.

EXAMPLE

One mole of an alkyl substituted diamine represented by the formula $R-NH-(CH_2)_3-NH_2$, wherein R is a linear alkyl radical containing 12 carbon atoms, was admixed, under mechanical agitation, with a sufficient amount of 80 Pale oil diluent to form a solution containing about 37.4 weight percent of said diluent. The alkyl substituted diamine employed was a commercially available compound known as Duomeen C.D. One mole of oleic acid was then added to the diamine containing solution. The reaction between the alkyl substituted diamine and oleic acid was carried out, under agitation, at ambient temperature for a sufficient period of time to allow formation of one mole of a alkyl substituted diamine monocarboxylate. (See Equation 1).

One mole of carbon disulfide was then added to the reaction mixture of the alkylsubstituted diamine monocarboxylate. The resulting reaction mixture was maintained at ambient temperature, under constant stiring, for an effective period of time to allow the carbon disulfide to react with the unreacted amine group of the alkyl substituted diamine monocarboxylate to produce one mole of an alkyl substituted diamine carboxylate dithiocarbamic acid. (See Equation 2).

The alkyl substituted diamine carboxylate dithiocarbamic acid produced above was then admixed with one equivalent weight of mercuric acetate. The reaction proceeded at a moderate rate and the temperature of the reaction mixture was controlled so that same was maintained at about 50° C. The reaction product, the mercuric salt of the dithiocarbamic acid, became black as the mercuric acetate was spent. (See Equation 3). Once the reaction had gone to completion, low molecular weight side-reaction products were removed by employing a vacuum on the reaction system while same was maintained at the reaction temperature and under vigerous agitation. The reaction product was then filtered and again vacuum stripped.

The recovered product, which had a high viscosity, was diluted then with kerosene to form analytical dilutions containing about 0.45 weight percent mercury. The samples were then stored for 6 weeks and again analyzed for mercury content. The mercury content was found to be analytically identical to the first analysis thus indicating the stability of the compositions of the present invention.

Having thus described the invention, I claim:

1. A stable oil-soluble analytical standard represented by the formula:

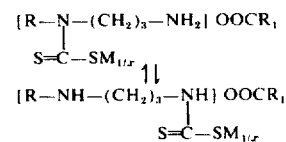

wherein M is a metal selected from the group consisting of mercury, vanadium, iron, lead, barium, berylium, tin, silver, titanium, copper, magnesium and sodium; R and $R_1$ are alkyl radicals containing from about 10 to 18 carbon atoms or mixtures thereof; and, $x$ is an integer equal to the chemical valance of M.

2. The composition of claim 1 wherein R is a mixture of linear alkyl radicals selected from the group consisting of saturated alkyl moieties and unsaturated alkyl moieties.

3. The composition of claim 2 wherein said alkyl radical is a saturated moiety selected from the group consisting of n-coco and n-tallow.

4. The composition of claim 2 wherein said alkyl radical is an unsaturated moiety selected from the group consisting of n-soya and n-oleyl.

5. The composition of claim 2 wherein $R_1$ is a linear alkyl radical.

6. The composition of claim 5 wherein M is mercury.

* * * * *